(12) United States Patent  
Fischer et al.

(10) Patent No.: US 6,286,722 B1
(45) Date of Patent: Sep. 11, 2001

(54) DELIVERY TIP LOCKING COLLARS AND RELATED SYSTEMS

(75) Inventors: Dan E. Fischer, South Jordan; Bruce S. Mclean, Sandy, both of UT (US)

(73) Assignee: Ultradent Products, Inc., Sandy, UT (US)

( * ) Notice: Subject to any disclaimer, the term of this patent is extended or adjusted under 35 U.S.C. 154(b) by 0 days.

(21) Appl. No.: 09/494,689

(22) Filed: Jan. 31, 2000

(51) Int. Cl.$^7$ .................................................... B67D 5/00
(52) U.S. Cl. ............................. 222/137; 222/567; 222/570
(58) Field of Search ..................................... 222/136, 137, 222/145.1, 145.3, 326, 327, 94, 566, 567, 570

(56) References Cited

U.S. PATENT DOCUMENTS

| | | | |
|---|---|---|---|
| Re. 36,235 | 6/1999 | Keller et al. | 222/137 |
| 4,767,026 | 8/1988 | Keller et al. | 222/137 |
| 4,979,942 * | 12/1990 | Wolf et al. | 222/137 |
| 4,981,241 | 1/1991 | Keller et al. | 222/137 |
| 5,038,963 * | 8/1991 | Pettengill et al. | 222/137 |
| 5,116,315 * | 5/1992 | Capozzi et al. | 222/137 |
| 5,137,182 | 8/1992 | Keller et al. | 222/153 |
| 5,290,259 | 3/1994 | Fischer | 604/218 |
| 5,301,842 * | 4/1994 | Ritter | 222/137 |
| 5,328,462 | 7/1994 | Fischer | 604/82 |
| 5,370,273 * | 12/1994 | Rohloff et al. | 222/137 |
| 5,609,271 | 3/1997 | Keller et al. | 222/145.6 |
| 5,643,206 | 7/1997 | Fischer | 604/82 |
| 5,665,066 | 9/1997 | Fischer | 604/82 |
| 5,697,903 | 12/1997 | Fischer | 604/82 |
| 5,918,772 | 7/1999 | Keller et al. | 222/145.6 |
| 5,975,367 * | 11/1999 | Coelho et al. | 222/137 |

* cited by examiner

*Primary Examiner*—J. Casimer Jacyna
(74) *Attorney, Agent, or Firm*—Workman, Nydegger & Seeley

(57) ABSTRACT

A delivery tip for delivering first and second materials has: (i) a hollow main body; and (ii) a septum extending along the length of the hollow main body, dividing the main body into first and second lumens. The first lumen terminates in a first opening on one side while the second lumen terminates in a second opening on an opposing side. The septum has a diverting end portion. First and second materials extend through respective first and second lumens of the tip until encountering the diverting end portion of the septum. The first and second materials then exit the tip in respective diverging first and second exit flow paths outwardly away from the distal delivery end of the delivery tip. A collar selectively mounts the delivery tip onto a two-part material delivery system. The collar can have a cap tethered thereto.

11 Claims, 8 Drawing Sheets

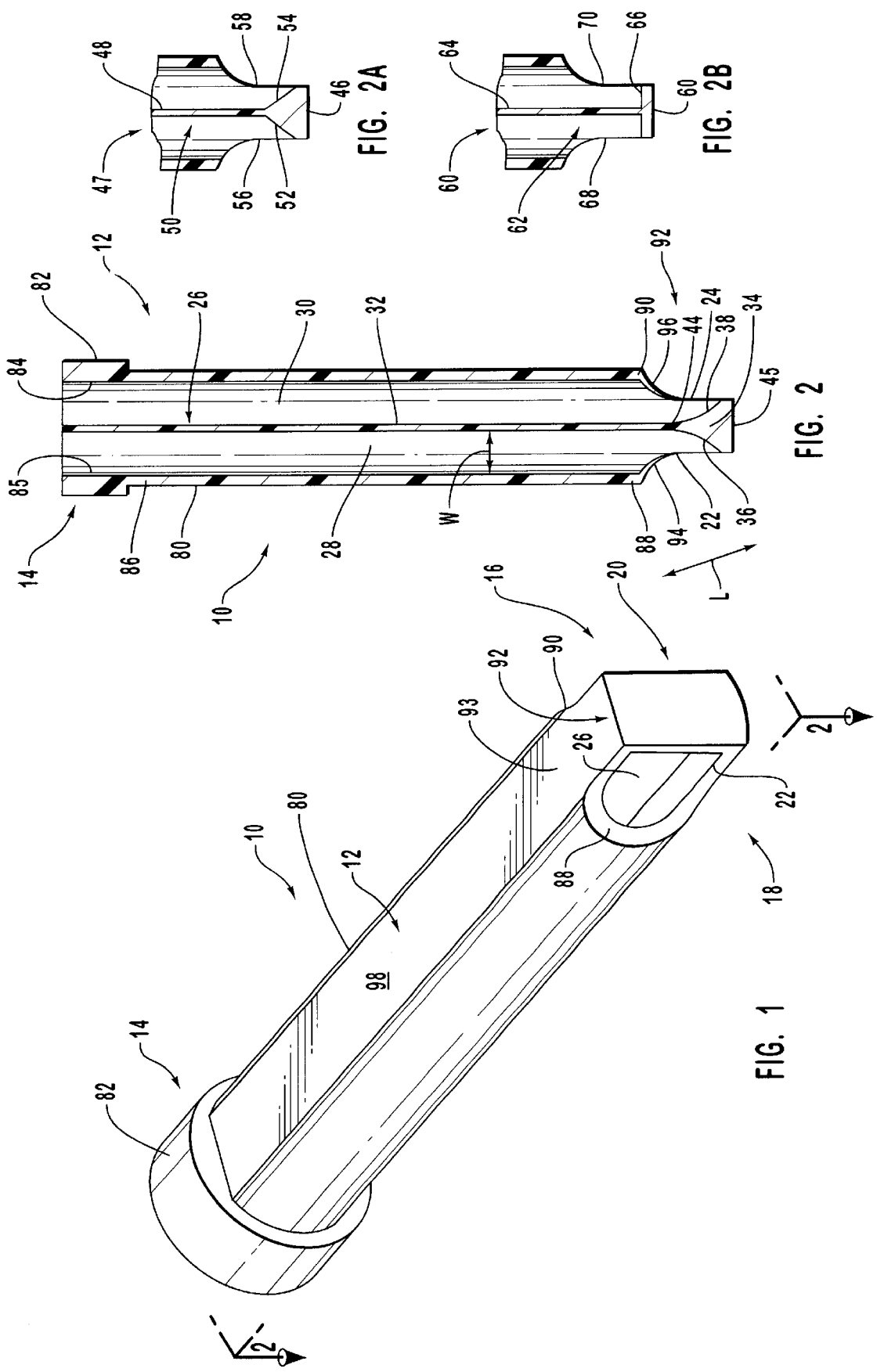

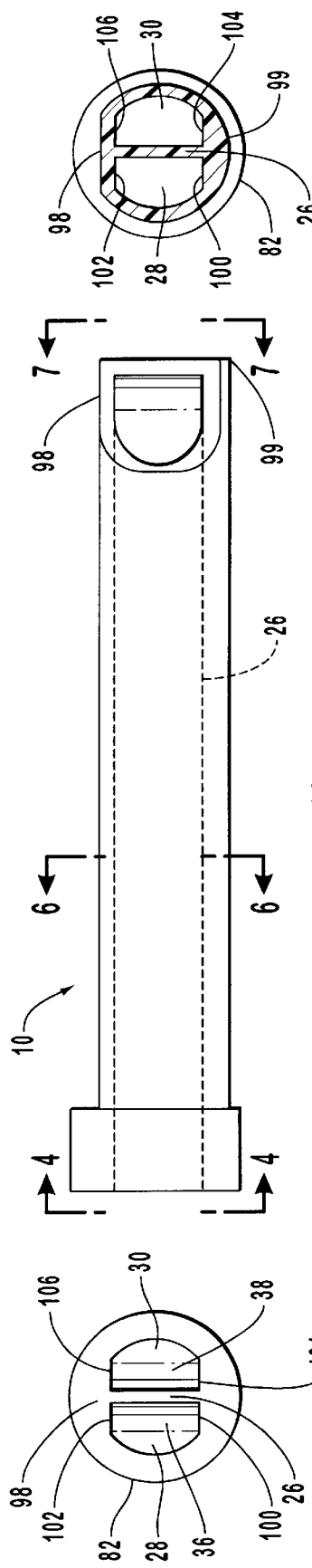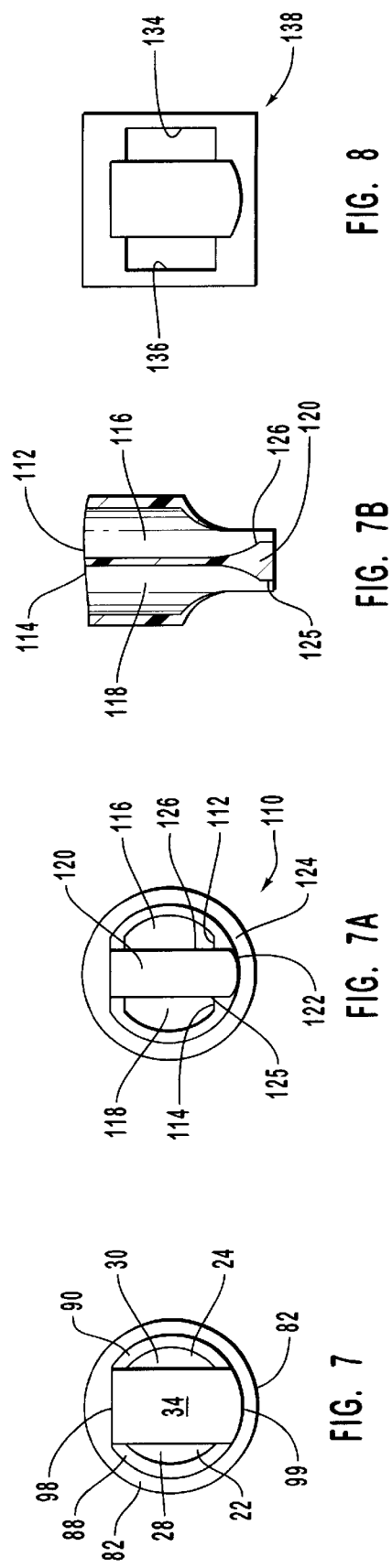

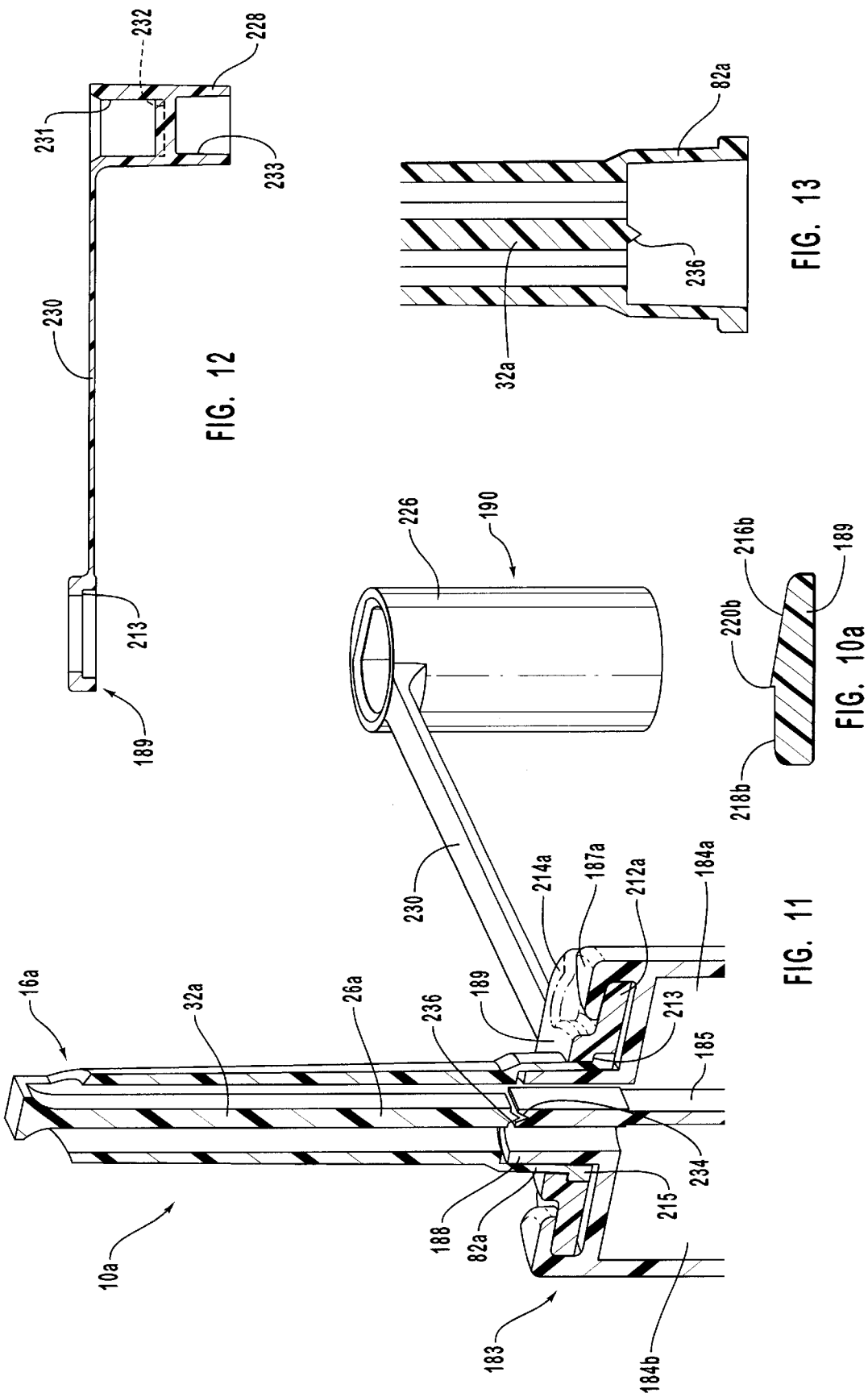

DELIVERY TIP LOCKING COLLARS AND RELATED SYSTEMS

BACKGROUND OF THE INVENTION

1. The Field of the Invention

This application is directed to methods and devices for delivering medical and dental compositions. More particularly, the application is directed to delivery tips for delivering multi-part medical and dental compositions and accessories relating thereto.

2. Relevant Technology

Many modern formulations are packaged in two parts, often known as "A/B components" or "first and second materials". Upon mixing, these A/B components typically undergo a chemical reaction which causes the resultant composition to "set up" in some desired manner, for example, by forming a hardened material. In the dental field, for example, several two-part formulations currently enjoy wide use, such as glass ionomer cements and resinous luting cements. Dental impression materials are also typically made using A/B components.

In order to function properly, it is important that the A/B components of these two component systems be separated until it is desired to mix the components. Typical techniques for retaining A/B type materials in a separated state before mixing the materials include loading the A/B materials into two-part material delivery apparatuses having separate side-by-side barrels or tubes. The side-by-side barrels are each configured to receive a separate material therein and deliver the separate material therefrom.

Examples of such two-part material delivery apparatuses having side-by-side barrels are disclosed in U.S. Pat. Nos. 5,290,259; 5,328,462; 5,643,206; 5,665,066; and 5,697,903, assigned to Ultradent Products, Inc., each of which are incorporated by reference herein.

A wide variety of such two-part material delivery apparatuses exist. Such apparatuses typically have a proximal material receiving end, and a distal delivery end. The distal delivery end typically features first and second openings which are adjacent one another and which are located at the end of neighboring barrels. Material delivered from one of the adjacent openings is typically delivered next to and in parallel relationship with the material delivered from the other opening.

Upon delivery of the first and second materials through the adjacent openings, the practitioner can then mix the materials in a mixing bowl, syringe, mixer or other device. Although mixing of the A/B materials is the ultimate goal of A/B type delivery systems, premature mixing and hardening of material is generally detrimental.

Nevertheless, in typical A/B type delivery systems, it is common for a certain amount of undesired commingling of A/B type materials to occur as the A/B materials exit the adjacent first and second openings. Sometimes, some of the mixed material contacts the distal delivery end of the delivery system, such as by depositing on one of the edges of the proximal and distal openings. Such mixed material tends to harden on the delivery system.

If mixed material hardens in an opening, the hardened material can block or impede the flow path of a barrel. The disruption of the normal flow pattern can cause additional mixing and hardening in undesired areas. Thus, the buildup of reactive A/B materials on the distal end of a delivery system can slow, stop, or otherwise disrupt the delivery of the materials through the system.

The problem of material build up becomes particularly acute when a delivery system is used, then temporarily set aside or stored before a subsequent use. This allows time for mixed materials to harden before the subsequent use.

Another problem associated with the delivery of A/B materials is that uncovered delivery ends can dry out or become inadvertently contaminated. While it is possible to cover delivery ends with a cap, such caps can become readily separated from the delivery system and lost. Furthermore, it can be difficult to achieve a reliable seal between a delivery tip and a two-part material delivery apparatus which delivers material to the delivery tip, thereby allowing seepage of material at the junction between the tip and the two-part material delivery apparatus.

There is, therefore, a need in the art for a system for delivering A and B type materials which keeps the materials separate until mixing is desired and thereby avoids cross-contamination and hardening of the materials until the desired time. Specifically, there is a need in the art for a system which avoids cross-contamination between an A and a B material at a distal delivery end of the system.

There is also a need in the art for an improved seal between material delivery systems and delivery tips. Furthermore, there is a need in the art for an improved system for covering the end of a delivery tip.

SUMMARY AND OBJECTS OF THE INVENTION

It is therefore an object of the invention to provide an improved delivery system for delivery of A/B type materials.

It is another object of the invention to provide an improved delivery tip for delivering A/B type compositions.

It is another object of the invention to provide an improved delivery tip for delivering separate A/B type compositions which prevents co-mingling of the separate A/B type materials until a certain, desired time.

It is another object of the invention to provide a delivery tip which delivers A/B type materials in separate lumens divided by a septum which prevents co-mingling of the A/B materials as the materials exit a distal delivery end of the delivery tip.

It is another object of the invention to provide an improved means for selectively coupling the delivery tip to a delivery means for delivering first and second materials to the delivery tip.

It is another object of the invention to provide an improved seal between a delivery tip and a delivery system.

It is another object of the invention to provide an improved cap for covering a delivery tip.

The delivery tip of the present invention delivers first and second materials along separate flow paths. The delivery tip comprises a hollow main body having a proximal receiving end and a distal delivery end. The distal delivery end of the hollow main body has (i) a first side; (ii) an opposing second side; (iii) a first opening at the distal delivery end on one side; and (iv) a second opening at the distal delivery end on the second side.

A septum extends within the hollow main body along the length of the hollow main body. The septum divides the main body into first and second lumens. The first lumen terminates in the first opening, and the second lumen terminates in the second opening.

The septum has (i) an elongate member; and (ii) a diverting end portion connected to the elongate member. The diverting end portion of the septum has first and second sides. The first side of the diverting end portion is located adjacent to the first opening. A second side of the diverting end portion is located adjacent the second opening.

Consequently, the first and second materials delivered to the proximal end of the hollow main body extend substantially linearly through respective first and second lumens until encountering the diverting end portion of the septum. Upon encountering the diverting end portion, the first and second materials exit in respective diverging first and second flow paths outwardly away from opposing sides of the distal delivery end of the delivery tip.

The diverting end portion of the septum is larger in width than the elongate member of the septum. The widened end portion of the septum causes material extending through the lumens to flow outwardly with respect to the longitudinal axis of the septum. This prevents first and second materials delivered from the respective lumens from intermingling with each other immediately upon delivery through the lumens. Instead, the materials are delivered separately and away from each other. The materials can then be combined by a practitioner through a variety of means, such as through the use of a mixing paddle, within a syringe, mixing bowl or dispensing device. Examples of such mixing paddles are disclosed in U.S. Pat. Nos. 5,328,462; 5,643,206; 5,665,066; and 5,697,903, which are incorporated by reference herein.

The relatively larger width of the diverting end portion of the septum can be achieved in a variety of different manners. In one embodiment, the sides of the diverting end portion each flare gradually outwardly with respect to the longitudinal axis of the septum such that the diverting end portion gradually widens from a proximal to a distal end of the diverting end portion. Such gradual widening can be achieved, for example, when the sides of the flared diverting end portion curve gradually from a proximal end of the diverting end portion to a distal end of a diverting end portion, forming a groove or chamfer.

Optionally, gradual widening of the diverting end portion from a proximal to a distal end of the diverting end portion can occur when the diverting end portion slants from a proximal end of the diverting end portion to a distal end thereof, each side slanting outwardly from a proximal to a distal end thereof. In yet another embodiment, the first and second sides flare outwardly by configuring the diverting end portion to be substantially transverse to the elongate member of the septum.

The proximal end of the hollow main body of the delivery tip is configured to be coupled to a delivery means for delivering first and second materials to the delivery tip, such as a two-part material delivery apparatus. In one embodiment, a collar is employed which selectively couples the delivery tip to the delivery apparatus.

The collar enables an improved seal between a delivery tip and a delivery means. In one embodiment, a cap for selectively covering the distal end of the delivery tip is tethered to the collar, thereby preventing the cap from being lost.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered to be limiting of its scope, the invention will be described and explained with additional specificity and detail through the use of the accompanying drawings in which:

FIG. 1 is a perspective view of a dual material delivery tip of the present invention.

FIG. 2 is a top cross sectional view of the delivery tip of FIG. 1.

FIG. 2A shows an alternate distal delivery end from that shown in FIG. 2.

FIG. 2B shows an alternate distal delivery end from that shown in FIG. 2.

FIG. 4 demonstrates a rear view of the delivery tip of FIG. 1.

FIG. 5 demonstrates a side view of the delivery tip of FIG. 1 featuring a lumen of the tip in phantom lines.

FIG. 6 features a cross sectional view of the main body of the delivery tip of FIG. 1.

FIG. 7 demonstrates a frontal view of the delivery tip of FIG. 1.

FIGS. 7A and 7B demonstrates views of an alternative delivery tip from that of FIG. 7.

FIG. 8 features a frontal view of an alternate delivery tip of the present invention having square or rectangular shaped lumens.

FIGS. 10 and 11 feature an example of an alternate two-part material delivery system.

FIG. 10a shows a cross sectional view of a portion of the collar shown in FIGS. 10 and 11.

FIG. 12 features an example of the collar of FIGS. 10 and 11 tethered to a cap of the present invention.

FIG. 13 features a cross sectional view of the proximal end of the delivery tip 8 featured in FIGS. 10 and 11.

DETAILED DESCRIPTION OF THE PREFERRED EMBODIMENTS

Figure 3:
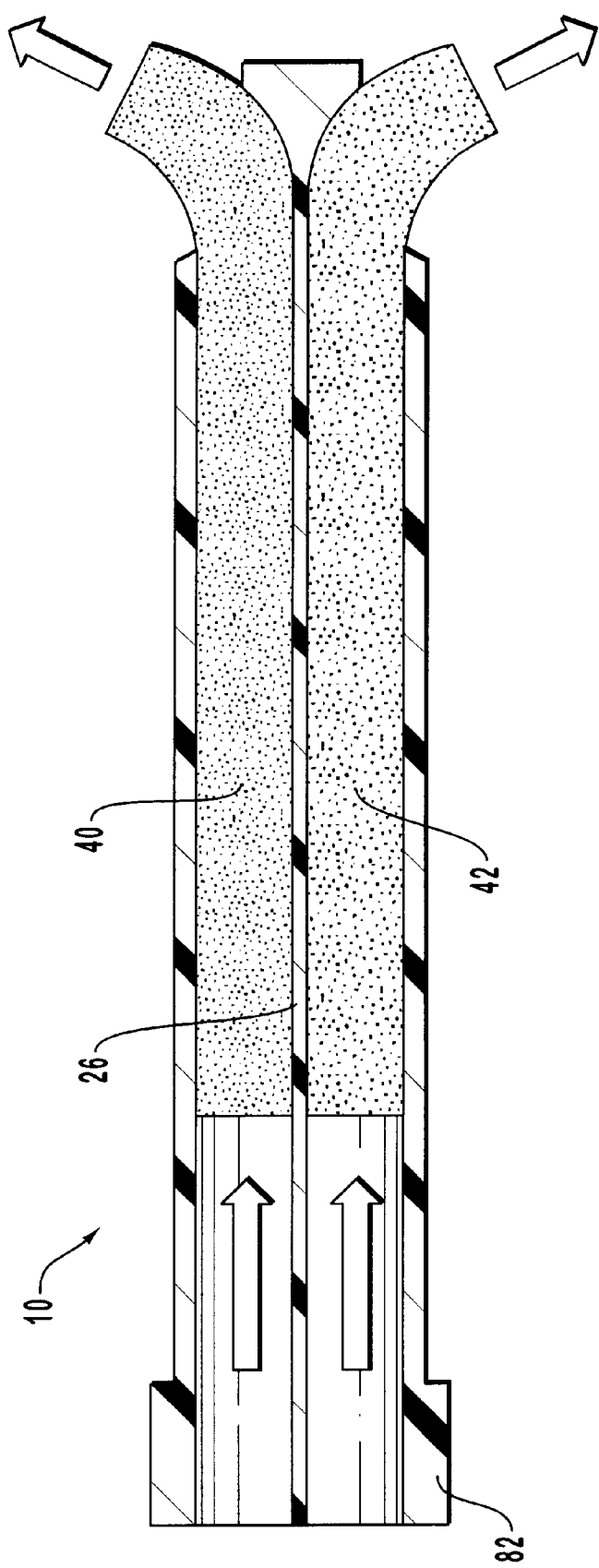
FIG. 3 features the delivery tip of FIG. 2 delivering first and second materials through opposing lumens thereof, demonstrating the diverging flow paths of the materials.

FIGS. 1–8 depict an example of a two-part material delivery tip at 10. The configurations of various embodiments of the two-part material delivery tip are discussed in detail in reference to these figures. The two-part material delivery tip is intended for use with a two-part material delivery apparatus. Accordingly, FIGS. 9A–9C, 10–11 and 13 each depict a two-part material delivery tip being used in combination with various embodiments of a two-part material delivery apparatus. As discussed in greater detail hereinbelow, each two-part material delivery apparatus disclosed herein is an example of a delivery means for delivering first and second materials to delivery tip.

With reference now to FIGS. 1 and 2, an example of a two-part material delivery tip 10 of the present invention is shown in a perspective view. Delivery tip 10 comprises a hollow main body 12. Main body 12 has a proximal receiving end 14 and a distal delivery end 16. Proximal receiving end 14 of body 12 is configured to be coupled to a delivery means for delivering first and second materials to delivery tip 10. Delivery tip 10 receives the first and second materials from the delivery means. Distal delivery end 16 has a first side 18 and a second side 20, and first and second openings 22, 24 at respective first and second sides 18, 20.

Delivery tip 10 further comprises a septum 26. Septum 26 extends within hollow main body 12 a long the length thereof. Septum 26 divide s main body 12 into first and second lumens 28, 30. First lumen 28 terminates in first opening 22 and second lumen 30 terminates in second opening 24.

Septum 26 has an elongate member 32 having a longitudinal axis and a diverting end portion 34 connected to elongate member 32 of septum 26. Diverting end portion 34 has a width which is greater than the width of elongate member 32, as shown in FIG. 2. Also as shown, a first side 36 of diverting end portion 34 is located adjacent first opening 22. A second side 38 of diverting end portion 34 is located adjacent second opening 24.

As a result of the configuration of delivery tip 10, first and second materials delivered to proximal end 14 of hollow main body 12 extend substantially linearly through respective first and second lumens 22, 24 until encountering diverting end portion 34 of septum 32. The first and second materials then exit in respective diverging first and second exit flowpaths outwardly away from opposing sides of distal delivery end 16.

A diverting end portion of the present invention can divert material out of the side openings in a variety of different manners. As noted above, the diverting end portion is wider than the elongate member of the septum. As one example, a diverting end portion has at least one side, and preferably first and second sides 36, 38 which flare outwardly with respect to the longitudinal axis of septum 26.

As shown in FIG. 2, diverting end portion 34 gradually widens from a proximal end 44 to a distal end 45 of diverting end portion 34 such that portion 34 becomes gradually wider than member 32. In the embodiment of FIG. 2, sides 36, 38 of diverting end portion 34 curve gradually from proximal end 44 to distal end 45 of diverting end portion 34 in a flared configuration. Sides 36, 38 are thus curved. However, a variety of different embodiments are available for flaring of diverting end portion 34 outward with respect to the longitudinal axis of the septum.

For example, as shown in FIG. 2A, in another embodiment of a distal delivery end 47 of a delivery tip, diverting end portion 46 extends from elongate member 48 of septum 50. Diverting end portion 46 has first and second sides 52, 54 each of which slant outwardly from a proximal to a distal end thereof such that portion 46 is wider than member 48. Slanting diverting end portion 46 is another example of a diverting end portion which gradually widens from a proximal to a distal end thereof.

In yet another embodiment of a septum having a diverting end portion which has a width which is greater than the width of the elongate member, and which flares outwardly with respect to the elongate member, septum 62 of distal delivery end 60, featured in FIG. 2B, has an elongate member 64 and a diverting end portion 66 which extends from member 64 and is disposed transversely to elongate member 64. In FIGS. 2A and 2B, as first and second materials extend along respective first and second lumens, the materials are either slanted outwardly by slanting sides 52, 54 through apertures 56, 58 (FIG. 2A), or contact transverse diverting end portion 66 and are then expressed outwardly from apertures 68, 70 (FIG. 2B).

With continued reference to FIGS. 1 and 2, hollow main body 12 comprises a body wall 80. At proximal end 14, body wall 80 is formed into a proximal, female, receiving portion 82. Interior surfaces 84, 85 of receiving portion 82 are configured to receive first and second distal tips, respectively, of the delivery means in mating relationship. In a preferred embodiment, the interior surfaces 84, 85 of receiving portion 82 have a slight internal taper (e.g., an approximately 1.7 degree taper) in order to mate with the delivery means in a fluid tight manner.

In one embodiment, the delivery means has first and second nipples or neck portions which mate with respective lumens in receiving portion 20. However, receiving portion 82 may receive a variety of different delivery means for delivering first and second materials to delivery tip 10.

Body wall 80 further comprises first and second distal shoulder portions 88, 90 and a narrow neck portion 92 extending distally from shoulder portions 88, 90. Neck portion 92 begins where shoulder portions 88, 90 terminate. As shown, body wall 80 tapers distally and inwardly from shoulder portions 88, 90 to form neck portion 92. Neck portion 92 is substantially thinner than shoulder portions 88, 90. Consequently, openings 22, 24 have sufficient size that materials exit rapidly, unencumbered, and outwardly upon reaching openings 22, 24.

In one embodiment, as shown in FIGS. 1 and 2, diverting end portion 34 is located within neck portion 92. Diverting end portion 34 is located distally from a portion 93 (FIG. 1) of wall 80 positioned between shoulder portions 88, 90. Thus, openings 22, 24 can release material even before material reaches diverting end portion 34. Material being released through an opening 22 or 24 is delivered separately and away from material within an opposing lumen. Since neck portion 92 tapers inwardly with respect to shoulder portions 88, 90, openings 22, 24 in neck portion 92 are not blocked by neck portion 92.

Another feature which assists in delivering material from openings 22, 24 without openings 22, 24 being blocked includes, in a preferred embodiment, that the distance measured by the length "L" of openings 22, 24 is greater than the distance measured by the width "W" of lumens 28, 30. Consequently, openings 22, 24 readily receive material therethrough and do not act as stops or constrictions for flowing material, but readily allow material flowing therefrom. The relative size of openings 22, 24 encourages any fragments or potential blockages to flow out of openings 22, 24, rather than being constricted therein. In addition, the greater length "L" also encourages the first and second materials to flow outwardly away from distal delivery end 16.

Also as shown in FIG. 1, wall 80 of body 12 preferably has a flat surface 98 on at least one portion thereof Flat surface 98 can be employed to support tip 10 on a support surface to thereby ensure that openings 22, 24 deliver to opposing substantially horizontal sides, rather than having one opening below another opening during delivery, which could potentially cause premature intermingling of materials exiting the openings. Flat surface 98 can also be used to ensure proper aligned mating with a cap, or other structure, for example.

With reference now to FIG. 3, first and second materials 40, 42 delivered to proximal end 14 of body 12 extend substantially linearly through respective lumens 22, 24, then exit in diverging first and second exit flow paths outwardly away from opposing sides of delivery tip end 16 of delivery tip 10. In the event of any blockage or contamination which happens to be delivered or formed in one of the lumens, apertures 22, 24 are oriented such that the blockage can be readily expressed therethrough.

With reference now to FIGS. 4–7, it is also desirable to configure lumens 28, 30, such that lumens 28, 30 have at least one flat surface, and preferably upper and lower flat surfaces 100, 102, and 104, 106 respectively. One advantage of flat surfaces 100, 102, and 104, 106 is that material flowing through respective lumens 28, 30 is not encouraged to clog into a small crevice or cavity.

As shown in FIGS. 4 and 6 for example, lumens 28, 30, preferably each have a generally simicircular, "D" shape having flat ends 100, 102 and 104,106, respectively. These flat ends 100, 102, 104, 106 are considered to be advantageous over sharp comers in the ends because material is significantly less likely to become lodged in ends 100, 102, 104, 106. Thus, lumens 28, 30 are less likely to clog than lumens having a semicircular shape with comers at the junctions between the arc and the flat portion at each end. Such comers tend to act as crevices in which clogs can more readily form.

As shown in FIGS. 5 and 6, an opposing end of body 12 from flat portion 98 features a rounded portion 99 of wall 80. However, a delivery tip of the present invention may have a variety of different configurations, such as a completely circular cross section or a cross section having one or more flat edges.

As shown in FIG. 4, the width of the flat surfaces 100, 102, 104, and 106 of lumens 28, 30 is the same width as that of sides 36, 38 of diverting end portion 34.

However, with reference now to FIGS. 7A and 7B, another embodiment of a delivery tip 110 is shown wherein the width of upper and lower flat surfaces 112, 114 of respective lumens 116, 118 is greater than the width of respective sides 125, 126 of diverting end portion 120. This can assist in preventing the formation of pockets or crevices in which material can become lodged, preventing flow. Diverting end portion 120 may be curved or slanted, as shown in FIG. 2 and FIG. 2A, or transverse as shown in FIG. 2B, or otherwise configured such that portion 120 is wider than an elongate member of a septum. Lumens 116, 118 can be rounded on the exterior portions thereof as shown in FIG. 7A or may be square or rectangular in shape as shown in the tip embodiment 138 of FIG. 8, which features flat exterior lumen portions 134, 136.

Delivery tip 10 and the other delivery tips disclosed herein may be used in a variety of different settings. For example, delivery tip 10 may be used to deliver a two-part material to a mixing bowl or pad after which a paddle or spoon is employed to mix materials. According to another technique, the two-part material is delivered through tip 10 to a syringe such as through a proximal or intermediate opening in the barrel of the syringe and is thereafter mixed with a mixing paddle for example. In another embodiment, the materials are placed directly on a spatula or mixing paddle and then mixed with another spatula or mixing paddle. A variety of other uses for delivery tip 10 may also be employed.

Figure 9A:
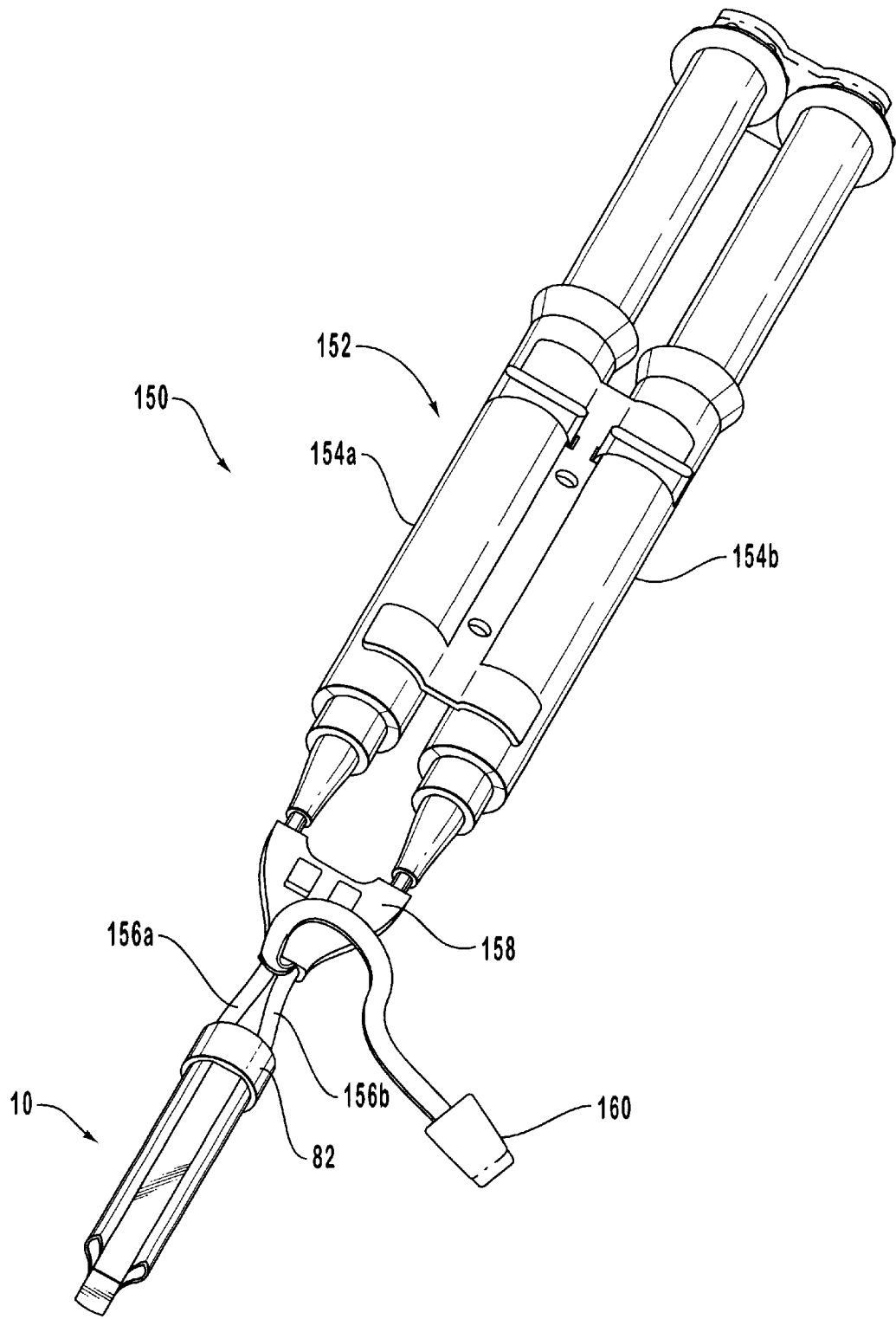
FIGS. 9A–9C feature examples of a two-part material delivery system.

As indicated above, FIG. 9A illustrates an example of a two-part material delivery system 150 of the present invention. System 150 comprises (i) delivery tip IO; and (ii) two-part material delivery apparatus 152. As also indicated above, apparatus 152 is an example of a delivery means for delivering first and second materials to delivery tip 10. A variety of different two-part material delivery apparatuses may be employed in the present invention as part of a two-part material delivery system 150.

Apparatus 152 comprises first and second barrels 154a, 154b and first and second respective delivery tubes 156a, 156b coupled in fluid communication thereto. Delivery tubes 156a, 156b are configured to be selectively coupled in fluid communication with proximal receiving end 82 of tip 10. Collar 158 holds tubes 156a and 156b together. Collar 158 also has a cap 160 tethered thereto for selectively covering the terminal ends of tubes 156a, 156b when tubes 156a, 156b are withdrawn from tube 10. Alternatively cap 160 or a similar cap is configured to cover the distal delivery end 16 of tip 10.

Side-by-side delivery of first and second materials is achieved through the use of dual-syringe system 150. For example, such side by side delivery of the first and second materials may include side-by-side loading of a syringe barrel, side by side delivery of first and second materials into a mixing bowl, or side-by-side loading into another container. Prior to use, syringe barrels 154a and 154b are filled with A and B components, respectively, of a two-component composition.

Figure 9B:
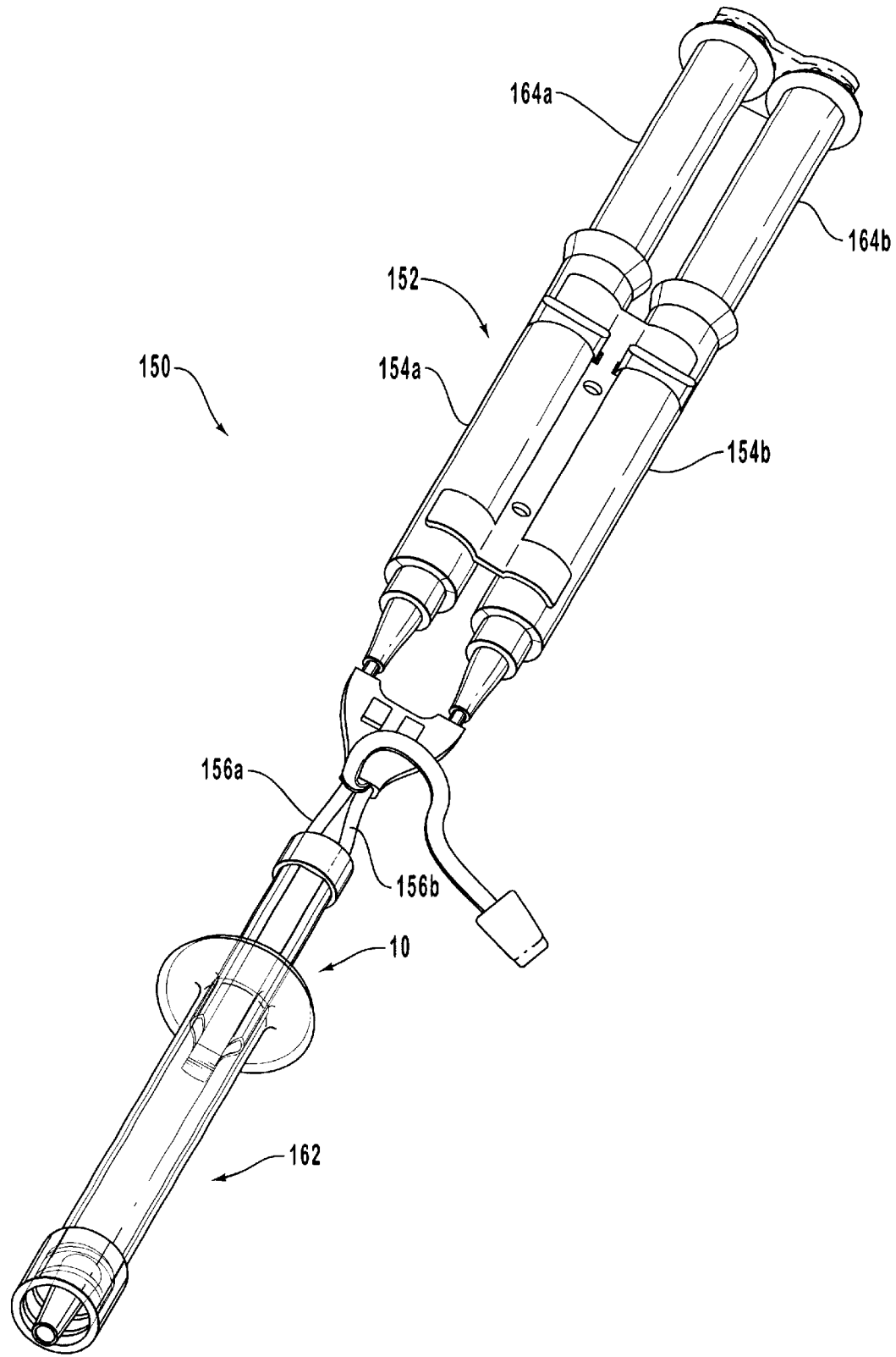

As shown in FIG. 9B, upon coupling tip 10 to delivery tubes 156a, 156b, tip 10 can then be positioned into a syringe barrel, such as barrel 162. Plungers 164a and 164b are then depressed into corresponding barrels 154a, 154b. In one embodiment, plungers 164a, 164b are depressed while slowly, simultaneously withdrawing tip 10 from within the inner chamber of barrel 162. This results in deposition of the first and second materials from respective syringe barrels 154a, 154b side-by-side within barrel 162. The materials can then be mixed, then delivered through barrel 162, for example.

Use of tip 10 protects the first and second materials within delivery tubes 156a, 156b and their corresponding syringe barrels 154a, 154b. Tip 10 ensures that first and second materials within system 150 remain separate during and after the delivery of some of the material from apparatus 152. Thus, the materials do not prematurely mix, even after storage of system 150 following an initial use.

Figure 9C:
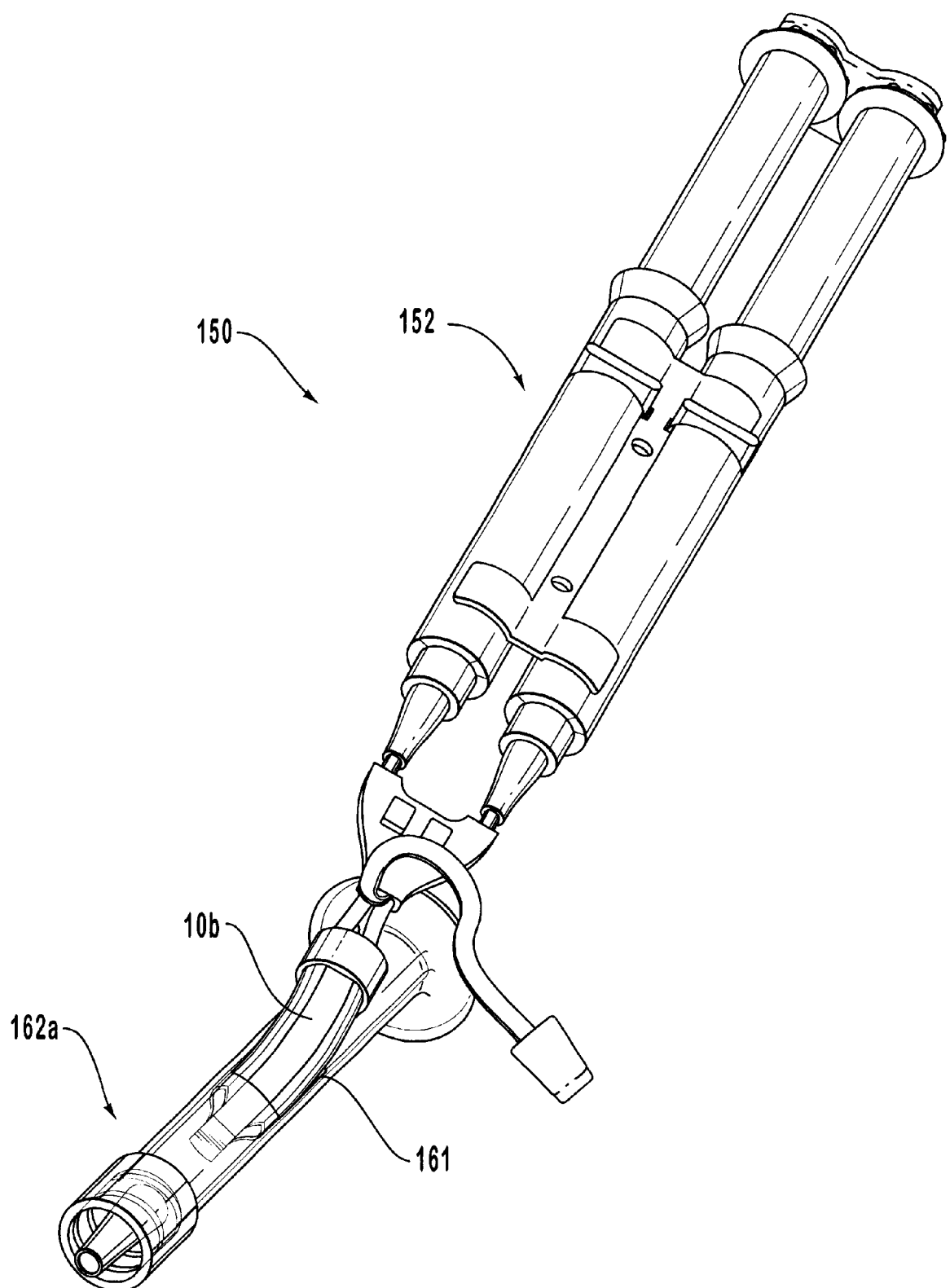

FIG. 9C illustrates an example of a flexible, elastomeric delivery tip 10b which can be selectively positioned within a side opening 161 of barrel 162a. First and second materials from apparatus 152 are delivered into barrel 162a through side opening 161. The materials are then mixed with a mixer and/or through the use of plunger. The tips of the present invention may thus be comprised of rigid or flexible materials, depending upon a desired use.

FIGS. 10–13 illustrate another example of a two-part material delivery system 180 of the present invention in an exploded view. System 180 comprises (i) delivery tip 10a; and (ii) two-part material delivery apparatus 182. Apparatus 182 is another example of a delivery means for delivering first and second materials to the delivery tip.

Two-part material delivery apparatus 182 comprises (i) a dual barrel cartridge 183 shown in cutaway, cross sectional view; and (ii) a dual plunger system 196, also shown in a cutaway, cross sectional view. Dual barrel cartridge 183 comprises first and second barrels 184a, 184b and first and second respective delivery tubes 186a, 186b coupled in fluid communication with respective barrels 184a, 184b. The respective barrels and tubes are separated by a septum 185. Tubes 186a, 186b have passageways which extend through opposing portions of neck 188 extending from respective barrels 184a, 184b. Tubes 186a, 186b are configured to be selectively coupled in fluid communication with proximal receiving end 82a of tip 10a. Claws 187a, 187b extend from respective barrels of cartridge 183.

In order to deliver first and second materials through barrels 184a, 184b, plungers 194a and 194b of plunger system 196 (or optionally, first and second separate plungers) are inserted into corresponding barrels 184a, 184b. In one embodiment, plungers 194a, 194b are depressed while slowly, simultaneously withdrawing tip 10a from within a container, such as a syringe barrel. Plunger system 196 selectively receives an insert 198 within a cavity 200 thereof. Insert 198 can be color coded, for example, to indicate that certain materials corresponding to the color are disposed within cartridge 183.

Collar 189 can be employed to selectively couple tip 10a to two-part material delivery apparatus 182. Claws 187a, 187b of cartridge 183, discussed above, selectively couple to collar 189. In order to couple tip 10a to apparatus 182, proximal end 82a of tip 10a can be mounted onto neck 188 of cartridge 183, after which collar 189 is selectively coupled to claws 187a, 187b.

Figure 10:
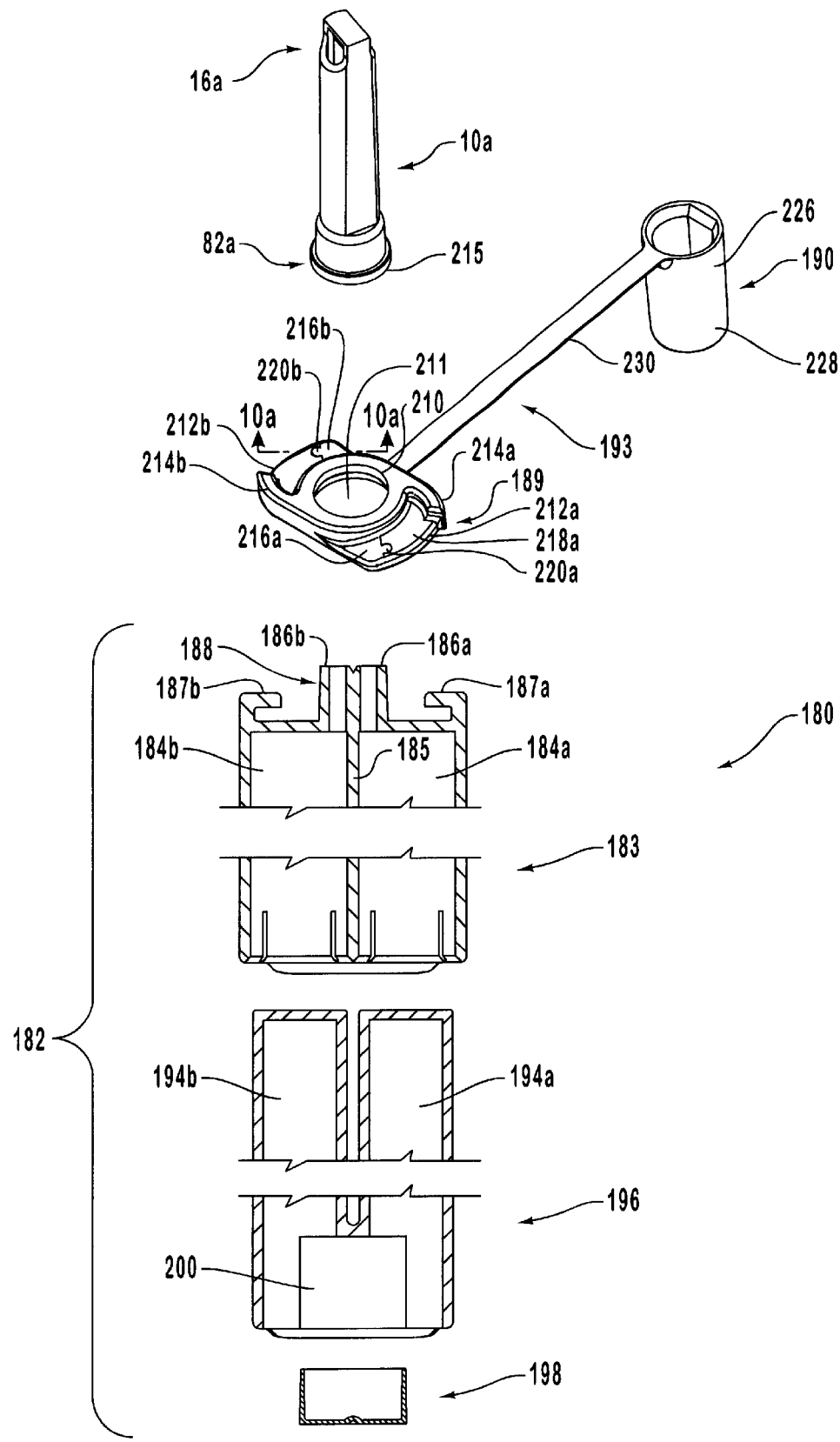

As shown in FIGS. 10 and 11, tip 10a can be coupled to cartridge 183 upon mounting proximal end 82a of tip 10a onto neck 188, then placing collar 189 over proximal end 82a of tip 10a, then turning collar 189 a quarter turn with respect to claws 187a, 187b, twisting the collar 189 under the claws 187a, 187b. Thus, claws 187a, 187b grasp the collar 189. Collar 189 thus tightly seals the connection between tip 10a and cartridge 183 such that material does not seep between the connection.

As shown in FIG. 10, in a preferred embodiment, collar 189 has a cap 190 tethered thereto for selectively covering distal delivery end 16a of tip 10a. Cap 190 can be used to keep first and second materials extruded into tip 10a, but not extruded out of tip 10a, fresh until it is desired to extrude these materials out of tip 10a. By tethering coupler 189 to cap 190, both functions can be performed by a single, conveniently unified device. This prevents cap 190 from becoming lost or misplaced. Collar 189, cap 190 and tether 230 form a convenient device 193 for selectively coupling tip 10a to two-part material delivery apparatus 182 and for selectively covering distal end 16a of tip 10a.

Coupling/covering device 193 will now be discussed in additional detail. Coupling/covering device 193 conveniently combines the advantages of a tip coupler, i.e. collar 189 with a tip covering device 190. Collar 189 is configured to selectively couple proximal end 82a of delivery tip 10a (or another delivery tip) to the distal end of cartridge 183. As shown, collar 189 selectively couples to one or more claws on the distal end of a two-part material delivery apparatus, such as apparatus 182.

With continued reference to FIGS. 10–11, proximal end 82a of delivery tip 10a selectively seats within collar 189. Collar 189 of FIGS. 10–11 comprises a hollow, circular coupler body 210 having opposing wings 212a, 212b extending therefrom. Hollow circular coupler body 210 defines an aperture 211 extending therethrough. Body further has an annular groove 213 therein (FIG. 11) which selectively mates with exterior annular ridge 215 of tip 10a.

As shown in FIGS. 10, 10a and 11, wings 212a, 212b extend from opposing exterior surfaces of coupler body 210. Stop ridges 214a, 214b are mounted on respective wings 212a, 212b and are configured to stop the movement of the wings as stop ridges 214a, 214b abut against respective claws. While a single stop ridge may be employed, two ridges are preferred.

Wings 212a, 212b each have a tapered portion 216a, 216b and a flat portion 218a, 218b. Opposing wings 212a, 212b of coupler 189 respectively are grasped by opposing claws 187a, 187b of cartridge 183 in the manner of a quarter turn fastener, the tapered portion of each wing sliding under the respective claw first, followed by the flat portion.

In one embodiment, such as shown in FIGS. 10 and 10a, at the interface between each tapered portion and each flat portion, each wing 212a, 212b comprises a barb ridge 220a, 220b extending gradually upwardly from the flat portion thereof. Barb ridges 220a, 220b are configured to abut claws 187a, 187b of cartridge 183 after the ridges 220a, 220b are slid under the claws 187a during assembly. Barb ridges 220a, 220b prevent or significantly impede the movement of the claws once the barb ridges are slid under the claws. While not required, barb ridges 220a, 220b can be employed in order to significantly increase the force required to dislodge wings 212a, 212b from respective claws 187a, 187b. A cross sectional view of a portion of collar 189 featuring barb ridge 220b is shown in FIG. 10a.

Each stop ridge 214a, 214b and each barb ridge 220a, 220b is an example of a means extending upwardly from at least one wing, for selectively abutting a portion (e.g., a claw) of a two-part material delivery apparatus contacting at least one wing.

As shown in FIG. 11, proximal end 82a of tip 10a selectively mounts on neck 188 of cartridge 183. A coupler selectively couples tip 10a to cartridge 183 by coupling first and second wings 212a, 212b to respective first and second claws 187a, 187b. Although less preferred, in one embodiment, the coupler and the cartridge may be configured so that the coupler has only one wing and the cartridge has one mating claw.

Proximal end 82a seats within coupler 189 by extending through hollow, circular coupler body 210 and mating with the interior surface thereof. Collar 189 couples distal tip 10a in fluid communication with cartridge 183 such that the barrels of cartridge 183 are in fluid communication with respective lumens of delivery tip 10a. Consequently, a first material in barrel 184a is not intermingled with a second material from barrel 184b until after the materials exit tip 10a and are mixed through the use of a mixer.

As shown in FIGS. 11 and 13, in order to ensure a seal such that the first and second materials remain in separate lumens and remain distinct from each other until after exiting distal end 16a of tip 10a, septum 26a of delivery tip 10a is configured to be coupled in mating relationship with septum 185 of cartridge 183. In the embodiment of FIG. 11, this mating relationship is achieved through the use of a groove 234 in septum 185 and a male member 236 of septum 26a extending from elongate member 32a of septum 26a. However, this may be accomplished in a variety of different manners such as by configuring septum 32a to have a female receiving portion or groove and septum 185 to have a male portion which mates therewith.

In one embodiment, the septums of the delivery tip and the dual barrel cartridge are compressed together. For example, the septums of the delivery tip and the dual barrel cartridge can be crushed together, e.g., the extending male portion can be crushed into the groove, to form a tight seal between the tip and the cartridge.

Cap 190 will now be discussed in additional detail with reference to FIGS. 10–12. Cap body 226 has a cavity 231 in an upper portion thereof which receives end 16a therein. Cap body 226 is configured to be selectively, removably mounted onto distal end 16a. In one embodiment, such as shown in FIG. 12, cavity 231 has a pointed ridge 232 in the central portion of the base thereof. Ridge 232 is designed to promote easy removal of cap 190 from distal delivery end 16a of tip 10a by contacting the most distal portion of end 16a with the pointed portion of ridge 232 only. However, cap 190 may also be employed without ridge 232. As another option, in one embodiment, a lower portion 228 of cap 190 also has a hollow cavity 233 therein. Tether 230 couples collar 189 to cap 190. Tether 230 is comprised of a flexible material such that cap 190 can be selectively mounted on distal end 16a of tip 10a. Tether 230 may have a variety of different configurations. Such configurations may include a cord, line, chain, wire, string or a rectangular member, for example.

Collar 189 is an example of an improved means for selectively coupling the delivery tip to a delivery means. The two-part material delivery tips disclosed herein, such as tips 10, 10a, 10b and the tips disclosed in FIGS. 2A, 2B, 7A, 7B and 8 are examples of means for receiving first and second materials into separate passageways and then directing the first and second materials out of the passageways. More particularly, the two-part material delivery tips disclosed herein, are examples of means for receiving first and second materials into separate lumens and then directing the first and second materials out of openings in the lumens.

In light of the numerous features of the delivery tips disclosed herein which enable A/B type materials to be deposited on opposing sides of the delivery tips, the delivery tips are highly efficient and prevent material in one lumen from co-mingling or polymerizing with material in another lumen. Thus, the material does not create clogs or other interruptions of the material flow. The diverting portions of the septums are wider than the elongate members of the septums, thereby forcing material from the lumens outwardly with respect to the longitudinal axis of the septums upon reaching the diverting portions.

The diverting end portions, such as portions 34, 46, 66, and 120 are examples of diverting means for diverting flow outwardly away from the longitudinal axis of the septum through the opposing first and second openings. A variety of other examples of such diverting means may be employed in the present invention, however, including another diverting end portion having a width which is greater than the width of the elongate member of the septum.

The delivery tips of the present invention and the collars and caps disclosed herein may be comprised of a variety of different suitable materials, such as polypropylene, polycarbonate, or polyethylene, thermosetting materials, thermoplastic elastomers, and neoprene, for example.

Other examples of delivery means for delivering first and second materials to a delivery tip are disclosed in U.S. Pat. Nos. 5,290,259; 5,328,462; 5,643,206; 5,665,066; and 5,697,903, assigned to Ultradent Products, Inc., each of which are incorporated by reference herein. A variety of other delivery means are possible, such as any two-part material delivery apparatus which is configured to deliver one material from one portion thereof and another material from another portion thereof.

The present invention may be embodied in other specific forms without departing from its spirit or essential characteristics. The described embodiments are to be considered in all respects only as illustrated and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A two-part material delivery system, comprising:
   means for receiving first and second materials into separate passageways and then directing the first and second materials out of the passageways;
   delivery means for delivering first and second materials to the means for receiving first and second separate materials into separate passageways and then directing the first and second materials; and
   means for selectively coupling the receiving and directing means to the delivery means, wherein the receiving and directing means comprises a two-part material delivery tip and wherein the means for selectively coupling and receiving the directing means to the delivery means comprises a collar, and further comprising a cap configured to selectively, removably cover the two-part material delivery tip, and wherein the cap is tethered to the collar.

2. A system as recited in claim 1, wherein the collar comprises:
   a hollow body portion configured to be disposed about a two-part material delivery tip; and
   at least one wing extending from the hollow body portion, the wing configured to selectively contact a portion of the delivery means.

3. A system as recited in claim 2, wherein the collar further comprises a ridge extending upwardly from the at least one wing, the ridge selectively abutting the portion of the two-part material delivery apparatus selectively contacting the at least one wing.

4. A system as recited in claim 3, wherein the ridge is selected from the group consisting of: (i) a stop ridge; and (ii) a barb ridge.

5. A system as recited in claim 1, wherein the delivery means comprises a dual barrel delivery system.

6. A system as recited in claim 1, wherein the collar comprises first and second wings extending from respective opposing sides of a hollow collar body, and the delivery means has a distal end with first and second claws, the first and second wings being configured to slide beneath respective first and second claws when the collar is mounted on the distal end of the delivery means and twisted with respect to the delivery means, the twisting of the collar thereby selectively coupling the delivery tip to the delivery means.

7. A two-part material delivery system, comprising:
   a two-part material delivery tip;
   a two-part material delivery apparatus configured to selectively deliver first and second materials to the two-part material delivery tip;
   a collar that selectively couples the two-part material delivery tip to the delivery means for delivering first and second materials to the delivery tip, the collar further comprising a cap comprising a main body, the main body of the cap configured to be selectively, removably mounted on a distal portion of the delivery tip, the cap being flexibly coupled to the collar.

8. A system as recited in claim 7, wherein the delivery tip is configured to be coupled in mating relationship with the delivery apparatus.

9. A system as recited in claim 7, wherein a septum of the delivery tip is configured to be coupled in mating relationship with a septum of the two-part material delivery apparatus.

10. A system as recited in claim 9, wherein a male portion of a septum of the delivery tip is configured to be coupled in mating relationship with a groove of a septum of the two-part material delivery apparatus.

11. A system as recited in claim 7, wherein the cap is coupled to the collar through the use of a flexible tether, the tether having a first end and a second end, the first end of the tether being coupled to the collar and the second end of the tether being coupled to the cap.

* * * * *

UNITED STATES PATENT AND TRADEMARK OFFICE
CERTIFICATE OF CORRECTION

PATENT NO.    : 6,286,722 B1
DATED         : September 11, 2001
INVENTOR(S)   : Dan E. Fischer; Bruce S. McLean It is certified that error appears in the above-identified patent and that said Letters Patent is hereby corrected as shown below:

Column 5,
Line 6, change "a long" to -- along --
Line 7, change "divide s" to -- divides --

Column 6,
Line 50, after "thereof" insert -- . --

Column 7,
Line 9, change "simicircular" to -- semicircular --
Lines 12, 15 and 17, change "comers" to -- corners --

Signed and Sealed this

Twenty-sixth Day of March, 2002

Attest:

*Attesting Officer*

JAMES E. ROGAN
*Director of the United States Patent and Trademark Office*